United States Patent [19]

Nomura et al.

[11] Patent Number: 5,493,897

[45] Date of Patent: Feb. 27, 1996

[54] GAS SENSOR

[75] Inventors: Tooru Nomura, Minoo; Yoshinobu Matsuura, Osaka; Tomohiro Inoue, Hyogo, all of Japan

[73] Assignee: Figaro Engineering Inc., Osaka, Japan

[21] Appl. No.: 383,217

[22] Filed: Feb. 3, 1995

[30] Foreign Application Priority Data

May 16, 1994 [JP] Japan ..................... 6-126890

[51] Int. Cl.⁶ ............... H05K 7/20; H05K 1/18; G01N 27/12
[52] U.S. Cl. ............ 73/23.2; 73/31.06; 29/840; 29/DIG. 10; 29/DIG. 38; 361/707; 361/807
[58] Field of Search ............... 73/23.2, 31.06; 29/831, 832, 840, DIG. 2, DIG. 10, DIG. 38; 361/388, 707, 417, 807

[56] References Cited

U.S. PATENT DOCUMENTS

| 4,204,248 | 5/1980 | Proffit et al. | 361/388 |
|---|---|---|---|
| 4,383,907 | 5/1983 | Legrand et al. | 204/426 |
| 4,445,256 | 5/1984 | Huguenin et al. | 29/25.35 |
| 4,751,611 | 6/1988 | Arai et al. | 361/421 |
| 5,095,404 | 3/1992 | Chao | 361/385 |
| 5,105,258 | 4/1992 | Silvis et al. | 357/71 |
| 5,134,463 | 7/1992 | Yamaguchi | 357/81 |
| 5,173,844 | 12/1992 | Adachi et al. | 361/414 |
| 5,311,404 | 5/1994 | Trask et al. | 361/762 |
| 5,326,936 | 7/1994 | Taniuchi et al. | 174/260 |
| 5,339,216 | 8/1994 | Lin et al. | 361/707 |
| 5,345,363 | 9/1994 | Bhattacharyya et al. | 361/749 |
| 5,363,278 | 11/1994 | Komorita et al. | 361/762 |
| 5,423,119 | 6/1995 | Yang | 29/841 |

FOREIGN PATENT DOCUMENTS 63-159744  7/1988  Japan.

Primary Examiner—Hezron E. Williams
Assistant Examiner—J. David Wiggins
Attorney, Agent, or Firm—Nikaido, Marmelstein, Murray & Oram

[57] ABSTRACT

An alumina substrate has a front surface with a semiconductor gas sensor main body attached thereon for specific detection of a surface exposed gas, and has a rear surface formed with a glass layer and a gold paste layer as superposed on the surface, and bonded to a gold plating layer on a frame by parallel gap welding. The gold paste layer is welded to the gold plating layer with the heat of welding. The glass layer prevents transmission of thermal impact of die bonding to the substrate.

7 Claims, 6 Drawing Sheets

GAS SENSOR

FIELD OF THE INVENTION

The present invention relates to gas sensors for detecting a combustible gas, toxic gas, water vapor or the like, and more particularly to die bonding for attaching the substrate thereof to a frame.

PRIOR ART

The present assignee has proposed die bonding of the rear surface of a gas sensor substrate to a frame (Unexamined Japanese Patent Publication No. 159,744/1988). In the case of such a gas sensor, a frame of 42 alloy or the like is coated with a die bonding material, i.e., glass paste, and placed on a sensor substrate prepared by dicing. The substrate is bonded to the frame by positioning a die bonding heater in intimate contact with the frame on one side thereof opposite to the substrate and melting the paste with the heat from the heater. The substrate is connected by wire bonding to frames other than the die bonding frame.

However, we have found that this technique of die bonding involves marked variations in die bonding strength and also in the wire bonding strength of the leads bonded to the electrode pads on the substrate. The variations in the die bonding strength are thought attributable to variations in the mode of heat transfer from the heater to the glass paste, and some bonds are extremely low in strength, substantially failing to serve as die bonds. Variations occur in the wire bonding strength when the heat applied for die bonding boils the glass paste, permitting the glass material to adhere to the electrode pad or organic residues of the vehicle to adhere to the pad. The adhesion of the glass material to the electrode could nullify the wire bonding strength almost completely.

SUMMARY OF THE INVENTION

In preparing gas sensors wherein the substrate is attached to a frame by die bonding, the primary object of the present invention is:

(1) to eliminate variations in the die bonding strength, (2) to obviate variations in the wire bonding strength, and (3) to prevent soiling of the sensor main body with the die bonding material.

A secondary object of the invention other than the foregoing is:

(4) to prevent the substrate from flawing during die bonding, (5) to obviate or diminish wire connection faults due to a fall or vibration, and (6) to make it possible to detect both gas and water vapor.

The present invention provides a gas sensor comprising a sensor main body formed on a ceramic insulating substrate, the substrate having a rear surface bonded to a frame, the gas sensor being characterized in that a metal layer is formed over the rear surface of the insulating substrate and welded to the frame. The metal layer is preferably a gold layer which is easily weldable to the frame. The gold layer is formed, for example, by printing and baking a gold paste, metallization of the substrate rear surface or gold plating. The metal layer need not always be of gold; a Pd layer or the like is also useful. Preferably, the frame is coated with a gold, Pd, Sn or like plating layer, which is welded to the metal layer over the substrate. The resulting weld has, for example, an Au—Pd, Au—Sn or Au—Au composition. The gas sensor can be fabricated by positioning the substrate rear surface in place relative to the frame, and passing a welding current through the frame, for example, by a parallel-gap welder to weld the metal layer to the frame with the heat generated.

It is desirable to provide a heat-insulating glass layer between the substrate rear surface and the metal layer. The glass layer is preferably approximately equal to the insulating substrate in coefficient of thermal expansion, and should be smaller than the substrate in thermal conductivity (e.g., one having up to $\frac{1}{3}$ of the thermal conductivity of the substrate). The substrate to be used is an alumina or like ceramic substrate. Alumina is inexpensive, has a low impurity content and high insulating properties and is therefore desirable. The glass layer is preferably 5 to 200 μm, more preferably 10 to 50 μm, in thickness. The glass layer is prepared, for example, by coating the substrate rear surface with a glass paste and baking the coating, or by affixing a thin sheet of glass, such as glass film, to the rear surface and melting the sheet by a heat treatment.

For the assembly of such a gas sensor, many frames, for example, are prepared and secured to a base. Electrode pads connected to the sensor body on the, substrate, i.e., pads connected to a gas sensitive film, for example, of a metallic oxide semiconductor and a heater film, are each connected to the desired frame. The metal layer over the substrate is bonded to the plating layer on one of the frames. The die-bonded frame need not always be wire-bonded.

Since the gravity on the substrate acts on the die-bonded frame, the frame is likely to deform when falling or when subjected to intense vibration to disconnect the bonded wire. To obviate the fault, it is desired to connect the die-bonded frame to another frame by a branch or to make the ratio of the loop height H of the wire to the loop length G not smaller than 0.5 to not greater than 1.3.

Preferably, the sensor main body has two gas sensitive films for detecting a gas and water vapor, respectively. These films are formed by the same kind of metallic oxide semiconductor. The metallic oxide semiconductor film for detecting water vapor is made sensitive substantially only to water vapor, for example, by covering the surface of the film with glass to restrict the contact of the film with the gas and causing the oxidizing activity of the film to burn a trace of gas penetrating into the film to remove the gas. In this case, the gas detecting metallic oxide semiconductor film and the water vapor detecting metallic oxide semiconductor film are of the same kind and can therefore be formed easily. The sensor thus integrated is used, for example, for controlling cooking devices such as microwave ovens.

According to the present invention, die bonding is effected by welding the metal layer to the frame. Since the weld formed is uniform, variations in die bonding strength diminish. In the case where the frame is coated with a glass paste for die bonding, the die bonding material is likely to sputter and adhere to electrode pads on the substrate, whereas the invention is free of such a likelihood to diminish variations in wire bonding strength. When the invention employs a glass layer which is prepared from a glass paste, the paste is completely baked before substrate dicing, so that the die bonding step will not soil the electrode pads or the gas detecting metallic oxide semiconductor film. Next, the glass layer, which is smaller than the ceramic insulating substrate in thermal conductivity, prevents a thermal shock due to die bonding from being transmitted to the substrate and cracking the substrate. The small thermal conductivity of the glass layer further reduces heat transfer from the substrate to the frame to decrease the power consumption of the sensor.

With a load acting on the frame to which the substrate is bonded, the frame deforms if subjected to a great impact as when falling. The deformation exerts an objectionable influence on the wire interconnecting the frame and the substrate, possibly causing a wire connection fault. The deformation of the frame and the resulting wire connection fault can be precluded by connecting the die-bonded frame to another frame with a branch. Wire connection faults can be obviated alternatively by making the ratio of the height H of the wire loop to the loop length G, i.e., H/G, not smaller than 0.5 to not greater than 1.3 to permit deformation of the loop and thereby prevent the connection fault due to the deformation of the frame. The deformability of the loop is dependent on the ratio H/G rather than the value H. If this ratio is at least 0.5, the frame deformation can be absorbed by the loop deformation, whereas ratios exceeding 1.3 entail the likelihood of contact between the wires, so that the preferred H/G ratio is 0.5 to 1.3.

Preferably, such a gas sensor comprises two metallic oxide semiconductor films of the same kind, one of which is covered with glass to serve as a water vapor sensitive element. Such a sensor is used, for example, for controlling a microwave oven by detecting the water vapor to be released upon thawing or reheating, or for detecting the combustible gas to be produced when food is heated on a grill or the like at a temperature of at least 150° C.

EMBODIMENTS

Embodiment 1

Figure 1:
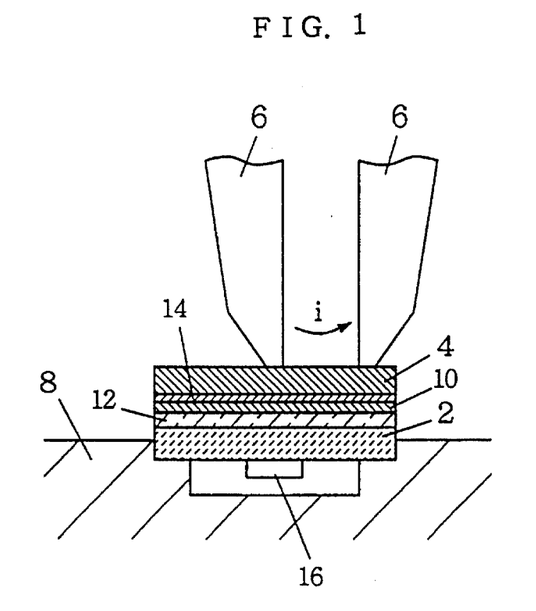
FIG. 1 is a sectional view of a gas sensor of first embodiment.
Figure 2:
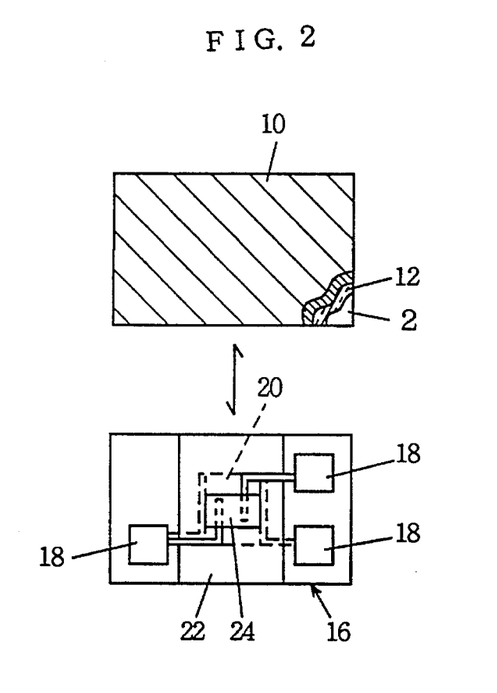
FIG. 2 is a diagram showing the substrate of the gas sensor.
Figure 3:
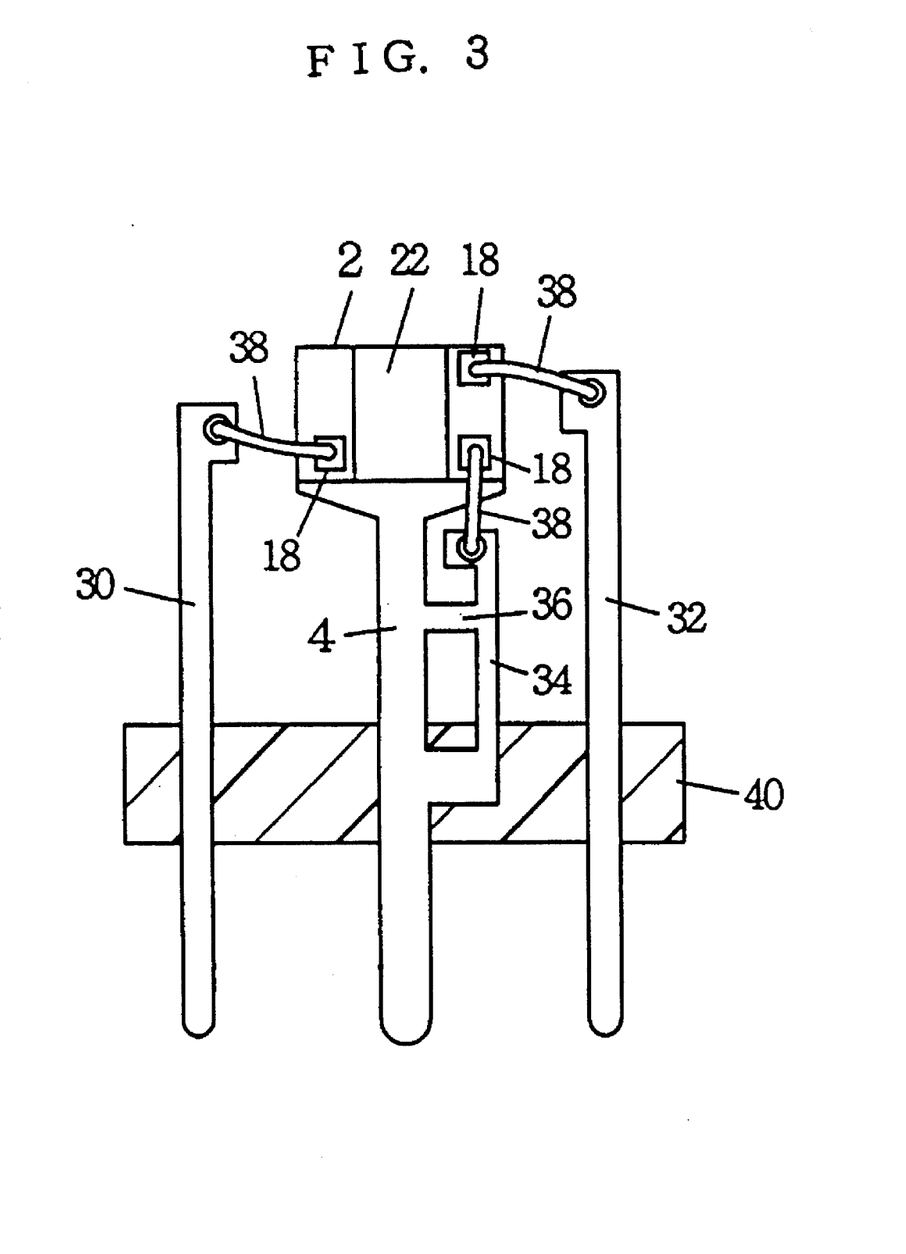
FIG. 3 is a fragmentary sectional view of the gas sensor.

FIGS. 1 to 3 show an embodiment. With reference to FIG. 1, indicated at 2 is a ceramic insulating substrate of alumina or the like. Also usable are mullite, spinel, etc. The substrate is a crystalline ceramic substrate. Indicated at 4 is a frame of 42 alloy or the like. A parallel gap welder has a pair of welding electrodes 6, 6 for passing thereacross a current i to weld the substrate 2 to the frame 4 by parallel gap welding. The drawing further shows a positioning jig 8 for die bonding, a metal layer 10 formed over the rear surface of the insulating substrate 2 and a glass layer 12 between the metal layer 10 and the substrate 2. The metal layer 10 is formed on the glass layer 12. The metal layer 10 is prepared by baking a gold paste in the present embodiment, and is preferably 0.5 to 30 μm in thickness. The thickness is 2 μm in the present case. Besides the gold paste, metallization or electroless plating can be resorted to for forming the metal layer 10. The layer 10 is made preferably of Au. Other materials usable are noble metals such as Pd, Rh and Pt, and base metals such as Ni and Cr. The glass layer 12 is preferably about 5 to about 200 μm, more preferably 10 to 50 μm, in thickness, and is comparable to the substrate in coefficient of thermal expansion. For example, the glass layer matches the substrate in coefficient of thermal expansion preferably with a difference of up to ±20%, more preferably up to ±10%. The glass layer 12 is smaller than the ceramic crystalline substrate 2 in thermal conductivity.

Indicated at 14 is a gold plating layer formed on a surface of the frame 4. Besides this layer, also useful is Pd plating, Ni plating, Sn plating or the like. The most preferred of these is the gold plating layer 14 as used in combination with the metal layer 10 of Au which is readily weldable. Indicated at 16 is a sensor main body provided on the front surface of the substrate 2.

FIG. 2 shows the front and rear surfaces of the insulating substrate 2. The substrate 2 is provided on its front surface with the sensor main body 16, which comprises three electrode pads 18, 18, 18, a heater film 20 of $RuO_2$ or the like, an insulating film 22 of $SiO_2$ or the like, and an $SnO_2$ film 24. The heater film 20 is formed as a lower layer, the insulating film 22 as an intermediate layer, and the $SnO_2$ film 24 as a surface layer. Connected to the heater film 20 and the $SnO_2$ film 24 are electrodes extending from the respective corresponding pairs of electrode pads 18. Although the $SnO_2$ film 24 is used for the present embodiment to provide a gas sensor, a humidity sensor is available by replacing the $SnO_2$ film 24 by a moisture sensitive film of proton conductor or the like which is operable at about 200° to about 400° C.

FIG. 3 shows the gas sensor as assembled. Besides the frame 4, the sensor has three other frames 30, 32, 34, which are connected to the respective electrode pads 18 by wire bonding with wires 38. The wire bonding provides a first bond, for example, on the frames 30, 32, 34, and a second bond on the electrode pads 18, whereas conversely the first bond may be provided on the pads 18 and the second bond on the frames 30, 32, 34. A resin base 40 for the sensor is molded integrally with the frames 4, 30, 32, 34 and has the frames 4, 34 united therein. The frame 4 having the substrate 2 bonded thereto is connected to the frame 34 by a branch frame 36 and is thereby prevented from deforming. The branch frame 36 need not always be provided. The branch frame 36 can be formed with extreme ease merely by modifying the etching pattern for preparing the lead frames from a thin metal sheet. The frames 4, 30, 32, 34 are originally lead frames interconnected by an unillustrated tiebar. The base 40 is molded before the frames are separated from the tiebar. The gas sensor additionally has a cap with a metal net, but the cap is known and therefore will not be described.

Test Example 1

One hundred gas sensors were prepared according to the embodiment of FIGS. 1 to 3. The frames 4, 30, 32, 34 were plated with gold over the entire surface to a thickness of 0.2

μm. A glass paste was printed on the rear surface of the insulating substrate 2 of alumina, 380 μm in thickness, and baked to form a glass layer 12. The material used was crossover glass PLS3310 (PLS3310: brand name) manufactured by Nippon Denkigarasu Co., Ltd. and comprising 11 wt. % of Si, 6.7 wt. % of Al, 8.2 wt. % of Mg, 2.5 wt. % of Ca, 2.5 wt. % of Na, 6.1 wt. % of Zn, 2.5 wt. % of Zr, 1.4 wt. % of Bi and the balance oxygen. The glass crystallizes when baked at 850° C. The glass layer 12 was given a thickness of 16 μm or 32 μm, and had a thermal conductivity of 0.03 J/(sec.cm.°C.) which was about 1/10 of the thermal conductivity of alumina, 0.3 J/(sec.cm.°C.). The thermal conductivity of the glass layer 12 used is a standard value for glass, is not particularly small but is yet about 1/10 of that of alumina. Use of the 16-μm-thick glass layer 12 reduces the heat loss from the frame 4 by about 1/3 since the layer is about 4% of the alumina substrate 2 in thickness and about 1/10 thereof in thermal conductivity. Use of the 32-μm-thick glass layer 12 reduces the heat loss from the frame 4 by about 1/2. The glass layer 12 had a coefficient of thermal expansion (coefficient of linear expansion) of $0.03 \times 10^{-4}$/°C., which approximately matched that of alumina with a difference of up to ±10% therebetween. A gold paste layer, 2 μm in thickness, was used as the metal layer 10. The paste was applied to the rear surface of the substrate and baked after baking the glass layer 12 and before fabricating the sensor main body 16. Sensor main bodies 16 were subsequently fabricated, and the substrate was diced into individual substrates 2.

The substrate 2 was set in a jig 8 to protect the sensor main body 16, the frame 4 was superposed on the substrate, and a welding current (1.3 KW in welding energy) was passed across the welding electrodes 6, 6 for parallel gap welding. The welding current, a.c. 60 Hz, was passed for 3 cycles (for 1/20 second). The heat generated by the current welded the metal layer 10 to the gold plating layer 14. When the two layers were separated at their interface and checked, the weld was found similar to a joint produced by thermocompression, and the variations in the welded state from sensor to sensor were found to be small. This is attributable to the fact that the metal layer 10 is welded to the gold plating layer 14 with the heat generated by the welding current. It is thought that the welding current passes partly through the gold plating layer 14 and partly through the metal layer 10. To give an enhanced die bonding strength, the parallel gap welding was done at two locations on the substrate 2 in the case of the present embodiment. The parallel gap welding was followed by wire bonding for connecting the electrode pads 18 to the frames 30, 32, 34 with wires 38 using a wire bonder. An Au wire, 30 μm in diameter was used for the wire bonding. The wire bonding was effected by thermosonic bonding to produce a first bond on the frames 30, 32, 34 and a second bond on the electrode pads 18. The frames 30, 32, 34 and the substrate 2 were heated to a temperature of 200° C. The bonding load was 70 g for both the first bond and the second bond. The ultrasonic energy input was 1 W for the first bond, and 3 W for the second bond. The order of the first bond and second bond may be reversed to produce the first bond on the pads 18. After wire bonding, the sensor was accommodated in a plastics housing and tested for die bonding and wire bonding strengths and for durability against falling.

As a comparative example, crystallized glass was used for die bonding according to Unexamined Japanese Patent Publication No. 159,744/1988. The substrate 2 used had the same construction as in the embodiment with the exception of not providing the glass layer 12 or metal layer 10. With a glass paste coating formed on the frame 4 and held in contact with the substrate 2, the frame 4 was heated to about 750° C. by a die bonding heater (separate from the heater 20), whereby the paste was melted and thereafter crystallized to bond the substrate 2 to the frame 4. The heating boiled the glass paste, causing the glass component and vehicle to partly flow to the sensor main body side of the substrate 2. The die bonding procedure was followed by wire bonding under the same conditions as in the above embodiment. Sensors (32 μm in the thickness of glass layer 12) of the embodiment were compared with those of the comparative example with respect to characteristics. Ten sensors of each of the embodiment and comparative example were checked for die bonding and wire bonding strengths.

The comparison in die bonding strength showed that with the embodiment, the average was about 4 Kgw with a strength distribution over the range of 3 to 5 Kgw. With the comparative example, the average was 3 Kgw and was not greatly different, but a strength distribution was found over the range of 0.5 Kgw to 5 Kgw and included extremely low die bonding strengths.

Next, the embodiment was compared with the comparative example in wire bonding strength. With the embodiment, the average was about 20 gw with a strength distribution over the range of 15 to 25 gw, whereas with the comparative example, the average was about 15 gw with a distribution range of 1 to 25 gw. The wire bond with a strength of up to 5 gw was substantially unserviceable as such, readily permitting disconnection of the wire when subjected to vibration or the impact of a fall. The wire bonds of very low strength included in the comparative example were found attributable to the fact that the glass in the die bonding glass paste or organic residue thereof flowed to the opposite side of the substrate 2 during heating to soil the electrode pad 18. We recognized this by microscopically observing the electrode pads 18.

Incidentally, the glass layer 12 used in the embodiment is prepared by printing on the rear surface of the substrate 2 and baking before dicing the substrate and before fabricating the sensor main body 16, so that the glass layer has been crystallized when the main body 16 or the pads 18 are formed, and is unlikely to soil these components.

Embodiment 2

Figure 4:
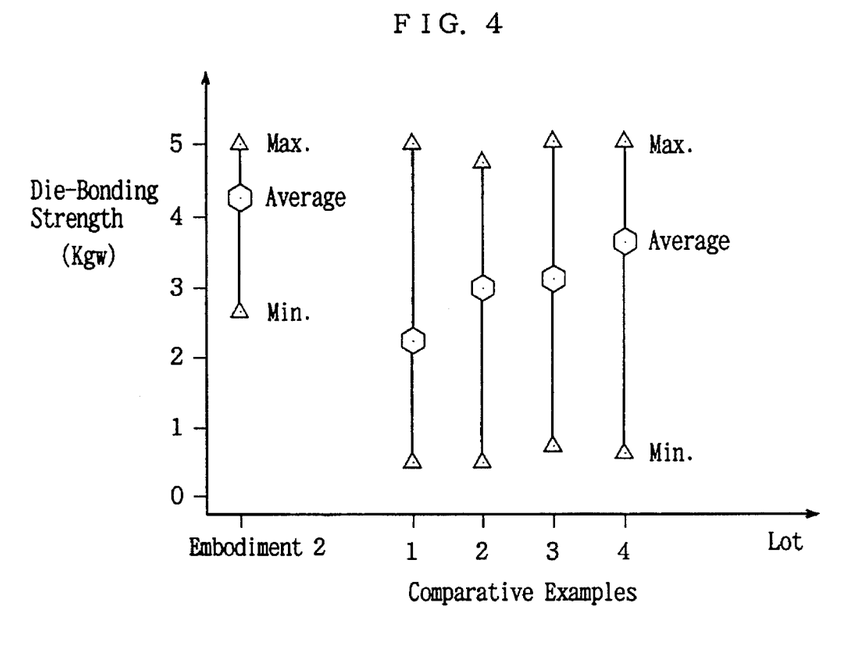
FIG. 4 is a characteristics diagram showing the die bonding strength of a sensor of a second embodiment.

As Embodiment 2, gas sensors were fabricated which had the same construction as Embodiment 1 except that the substrate 2 was a 500-μm-thick alumina sheet, had no glass layer 12 and was covered with a 10-μm-thick gold paste layer as the metal layer 10. As a comparative example, gas sensors were prepared according to the foregoing publication No. 159,744/1988. FIG. 4 shows the die bonding strength of the embodiment and the comparative example. The sensors were prepared in lots of 10 sensors each. The diagram shows the average, maximum and minimum of die bonding strengths. The values shown were calculated with the maximum of die bonding strengths taken as 5 kgw.

The die bonding strengths attained by Embodiment 2 are at least 2.7 kgw, with an average in excess of 4 kgw. With the comparative example, on the other hand, the die bonding strengths are low in average and include values of lower than 1 kgw which indicate a substantial failure in die bonding. This is due to uneven transfer of heat from the die bonding heater to the glass paste, which in turn appears attributable to the state of contact between the frame 4, glass paste and insulating substrate. With the comparative example, the minimum of die bonding strengths is small, leading to the low average. The die bonding strength is preferably at least 1 kgw, more preferably at least 1.5 kgw.

Figure 5:
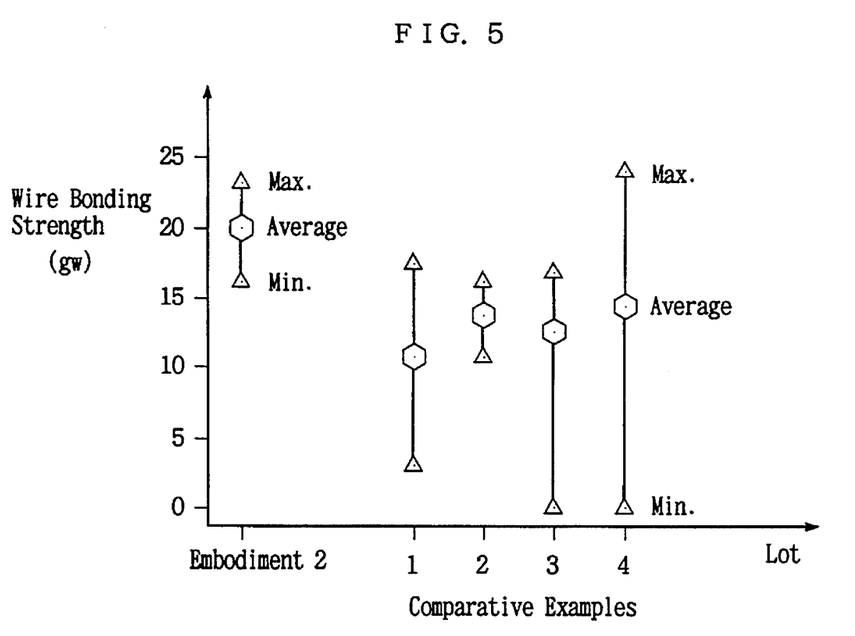
FIG. 5 is a characteristics diagram showing the wire bonding strength of the sensor of the second embodiment.

FIG. 5 shows the wire bonding strengths attained by Embodiment 2 and the comparative example. The sensors were prepared in lots of 10 sensors each. The diagram shows the average, maximum and minimum of wire bonding strengths. The sensors of Embodiment 2 exhibit wire bonding strengths the average, minimum and maximum of which are about 20 gw, 16 gw and 23 gw, respectively, and which involve small variations and are great on the average. In contrast, the sensors of the comparative example differ greatly in wire bonding strength except for Lot 2, some are less than 5 gw in this strength, and the average strength is also small. The wire bonding strength should preferably be at least 5 gw, more preferably at least 10 gw.

Aside from the foregoing characteristics, we checked gas sensors of Embodiment 2 and the comparative example for characteristics upon lapse of 40 days and found that the comparative example involved great drift with time. Presumably, the reason is that the glass material sputtering during die bonding flows onto and adheres to the $SnO_2$ film 24, soiling this film and other components.

Test Example 2

Gas sensors of Embodiment 1 were compared with those of Embodiment 2. In fabricating the gas sensors of Embodiment 2 wherein the glass layer 12 was not provided, die bonding was effected with welding energy of 1.3 KW, followed by wire bonding. The alumina substrate 2 was 380 μm in thickness. As in Test Example 1, the welding current was passed for a period of time corresponding to 3 cycles of 60 Hz (1/20 second). This welding condition was used also in the following procedures. Although Embodiments 1 and 2 were comparable in die bonding and wire bonding strengths, 13 out of 100 substrates 2 cracked during die bonding in the case of Embodiment 2. When the welding energy was reduced to 1.0 KW, cracking no longer occurred, but the die bonding strengths decreased to 1.5 Kgw on the average and had a lowered distribution range of 0.3 to 4.0 Kgw. Further when the alumina substrate 2 of Embodiment 2 was given an increased thickness of 500 μm, die bonding entailed no cracking, whereas the power required for heating the sensor main body 24 to 450° C. increased from 500 mW to 600 mW. With Embodiment 1, on the other hand, none of 100 substrates cracked during die bonding regardless of whether the glass layer 12 was 16 μm or 32 μm in thickness. The substrate 2 can be prevented from cracking by the glass layer 12 presumably because the heat insulating properties of the glass layer 12 blocked the transmission of thermal impact of die bonding to the alumina substrate 2. The power required for heating the sensor main body 24 to 500° C. was about 450 mW when the glass layer 12 was 16 μm thick or about 400 mW when the layer was 32 μm thick, hence reduced power consumption. This is because the glass layer 12 had about 1/10 of the thermal conductivity of the alumina substrate 2 and diminished release of heat through the frame 4.

Test Example 3

Figure 7:
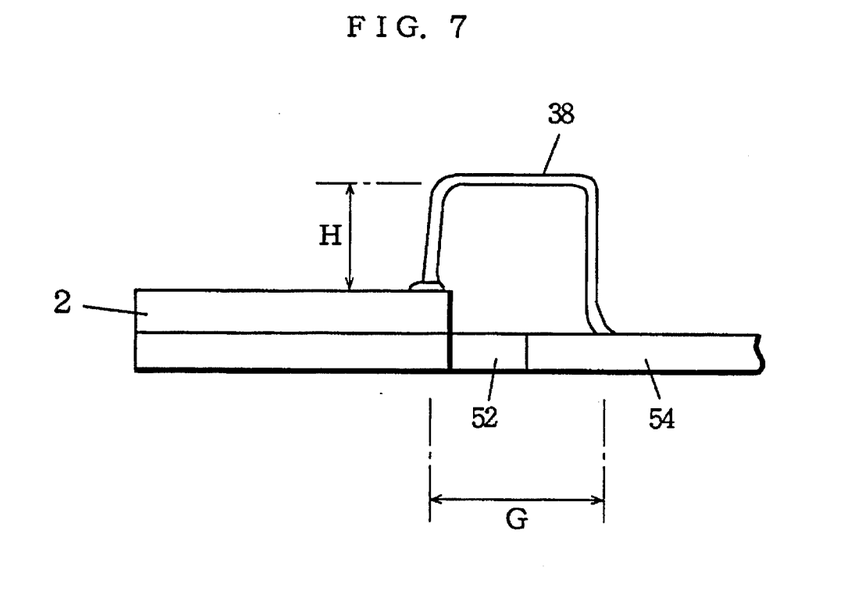
FIG. 7 is a fragmentary side elevation of the gas sensor of the third embodiment.

Two types of gas sensors were fabricated according to Embodiment 1; one not having the branch frame 36, and the other having the branch 36. One hundred sensors of each type were prepared, tested by being allowed to fall onto a concrete floor from a level 1 m thereabove (number of falls: 10) and then checked for the resulting fault. The two types of sensors were identical except the presence or absence of the branch frame 36 and were about 1 mm in loop height H and 1.5 mm in loop length G. FIG. 7 shows the definition of the loop height H and loop length G.

With the embodiment of the type wherein no branch frame 36 was provided, 23 out of 100 sensors developed a bonding wire connection fault at the first bond or second bond, but no break was found at an intermediate portion of the wire 38. The sensor wherein even one wire 38 developed a connection fault was taken as faulty in counting the number of faults. With the sensor having no branch frame 36, the substrate 2 was found tilted with the frame 4 twisted. In contrast, with the embodiment having the branch frame 36, none of the 100 sensors developed a wire connection fault. The reason why the frame 4 is twisted in the embodiment with no branch frame 36 is presumably that since the substrate 2 is under gravity, acceleration due to the impact of fall exerts a great force on the frame 4. If the frame 4 is twisted, tilting the substrate 2, an objectionble force acts on the wire 38 to release the wire from the bond. On the other hand, the fact that the embodiment having the branch frame 36 was free of wire connection faults is thought attributable to the branch frame 36 connecting the frame 4 to the frame 34 and serving as a kind of clamp or beam to prevent the deformation of the frame 4.

Most Preferred Embodiment (Embodiment 3)

Figure 6:
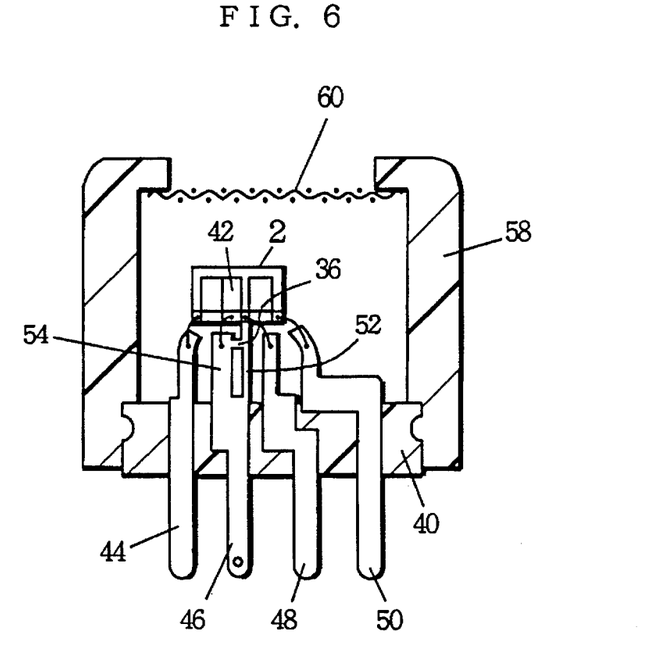
FIG. 6 is a sectional view of the gas sensor of a third embodiment.
Figure 8:
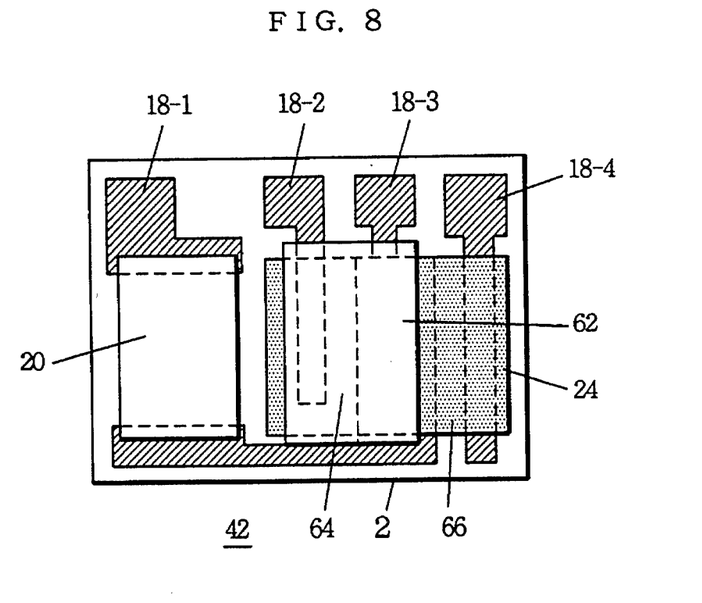
FIG. 8 is a plan view of the sensor main body of the third embodiment.

FIGS. 6 to 8 show a gas sensor for controlling cooking devices such as microwave ovens. With reference to FIG. 6 showing the construction of the sensor, a substrate 2 is provided with a sensor main body 42 which has a water vapor detecting portion, gas detecting portion and heater as integrated and which is connected to frames 44, 46, 48, 50 by wire bonding. The frame 46 has subframes 52, 54. The substrate 2 is attached by die bonding to the subframe 52, which is connected to the subframe 54 by a branch 36. Although the subframe 54 is wire-bonded and the subframe 52 die-bonded, the die-bonded subframe 52 may also be wire-bonded. The subframe 54 serves to reinforce the subframe 52 through the branch 36. The sensor is accommodated in a housing 58 made of a plastics or the like and having a metal net 60 for admitting a gas or water vapor therethrough.

FIG. 7 illustrates the meanings of the loop height H and loop length G. The loop height H is the height of the highest portion of the illustrated loop from the bonding face (substrate face) providing the first bond. The loop length G is the distance between the positions of the first and second bonds along a horizontal plane, i.e., the distance therebetween as projected on a plane parallel to the substrate 2. The length G is 1.5 mm in the present embodiment. The ratio H/G represents the degree of play of the loop, in other words, allowable deformability of the loop. The greater the ratio H/G, the more readily is the loop deformable. In the case of usual wire bonding, the loop height H is about 0.3 to about 0.5 mm, and H/G is about 0.2 to about 0.3. When H/G is great, the loop is susceptible to deformation. If the loop is then pulled on deformation of the subframe 52, the bulge of the loop deforms to a flat form to preclude a connection fault, while if compressed, the bulging loop becomes protuberant and is prevented from disconnection. To obviate wire connection faults, the value of H/G is preferably 0.5 to 1.3. When this value is at least 0.5, a decreased wire connection fault ratio will result, and when it is up to 1.3, contact between the wires 38 is avoidable.

FIG. 8 shows the construction of the sensor main body 42. A heater film 20 and $SnO_2$ film 24 are printed on a substrate 2, and the $SnO_2$ film is partly covered with a glass film 62. Four electrode pads 18-1 to 18-4 are provided, among which the pad 18-3 serves as a common pad and has its electrode connected to the films 20, 24. The portion of the $SnO_2$ film covered with the glass film 62 and positioned between the electrodes connected to the pads 18-2, 18-3 provides a water vapor detecting portion 64. This is because the glass film 62 restricts diffusion of gas and water vapor, a very small amount of diffused combustible gas is oxidized by the catalytic activity of the $SnO_2$ film 24, and the $SnO_2$ portion beneath the glass film 62 becomes sensitive only to water vapor. Water vapor diffuses into the water vapor detecting portion 64 from the other portion of the $SnO_2$ film 24 left uncovered with the glass film 62. The uncovered portion of the $SnO_2$ film 24 is sensitive to a combustible gas to serve a gas detecting portion 66. The water vapor detecting portion 64 is useful for controlling microwave ovens or like cooking devices in reheating food or thawing frozen food by detecting the water vapor released during heating or thawing. The gas detecting portion 66 is useful for detecting the combustible gas to be released when the surface of food being cooked on a grill or the like is heated to about 200° C.

The gas sensor of FIGS. 6 to 8 was fabricated in the following manner. A 32-μm-thick glass layer 12 (of the aforementioned material, PLS3310) was formed on the rear surface of a substrate 2. A metal layer 10, 2 μm in thickness, was formed as superposed on the layer 12 by baking a gold paste. Next, pads 18-1 to 18-4 and gold electrodes connected thereto were printed on the front surface of the substrate 2, followed by printing and baking of a heater film 20 of ruthenium oxide and further by printing of an $SnO_2$ film 24 and baking at 700° C. The surface of the $SnO_2$ film 24 was partly covered with a glass film 62 of Zn—Al—Mg—Si—B crystallized glass manufactured by Nippon Denkigarasu Co., Ltd., PLS3304 (brand name), followed by baking at 850° C. and then by dicing to obtain a sensor main body 42.

The substrate 2 (2.2×3.2 mm, 380 μm in thickness) provided with the sensor main body 42 was bonded to a subframe 52. The subframe 52 had at its one end a rectangular support portion of the same size as the substrate 2, and the frames 44 to 50 were plated with gold to a thickness of 1.0 μm. Die bonding was effected by parallel gap welding as shown in FIG. 1 using a.c. of 60 Hz for the period of 3 cycles (½₀ second) to apply welding power of 1.3 KW. Subsequently, the frames 44, 48, 50 and subframe 54 and the electrode pads 18-1 to 18-4 were interconnected with Au wires 38, 30 μm in diameter, by thermosonic bonding. In this wire bonding, a first bond was produced on the pads 18-1 to 18-4 at a substrate temperature of 200° C. with a bonding load of 70 g and energy of 1 W, and a second bond on the frames 44, 48, 50 and subframe 54 at a frame temperature of 200° C. with a bonding load of 70 g and energy of 3 W.

Figure 9:
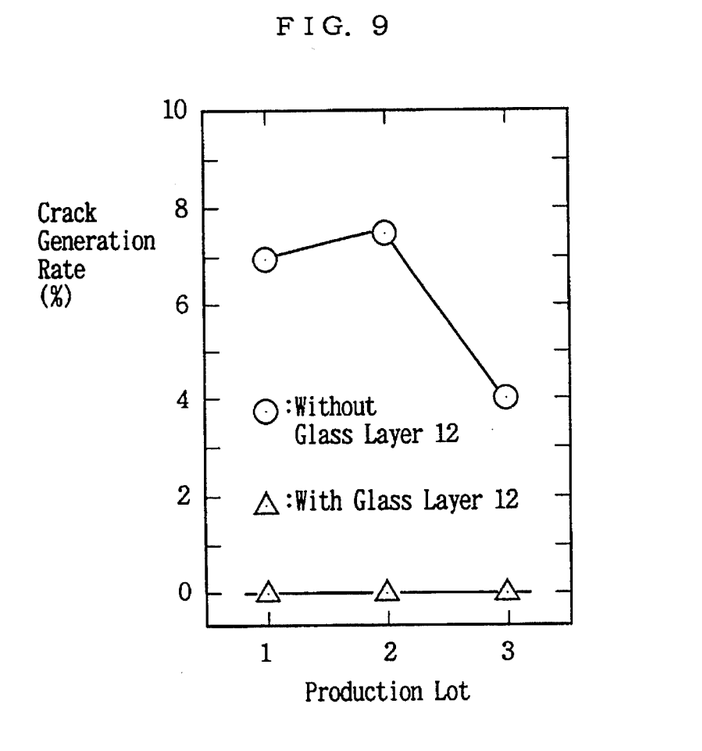
FIG. 9 is a characteristics diagram showing changes in crack generation rate due to the absence of a glass layer 12 from the third embodiment.

FIG. 9 shows the rate of cracking resulting from the die bonding. Although Embodiment 3 was found free of cracking, cracking occurred in 4 to 7% of the gas sensors not having the glass layer 12.

Figure 10:
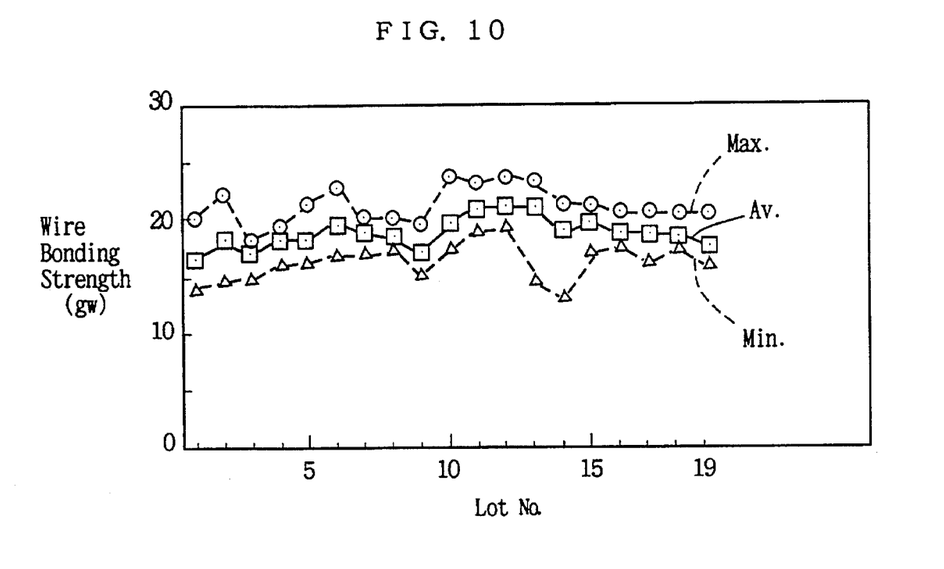
FIG. 10 is a characteristics diagram showing wire bonding strength distributions as determined for sensors of the third embodiment.

FIG. 10 shows wire bonding strength distributions of Embodiment 3. When the loop height H was reduced from 1.0 mm (loop length G: 1.5 mm, H/G: 0.67) to 0.5 mm (H/G: 0.33), the average of wire bonding strengths decreased to about 13 g. FIG. 10 shows the wire bonding strength averages and distribution ranges determined for 19 lots (10 sensors each). The averages are 15 to 20 g, hence a narrow distribution range.

Figure 11:
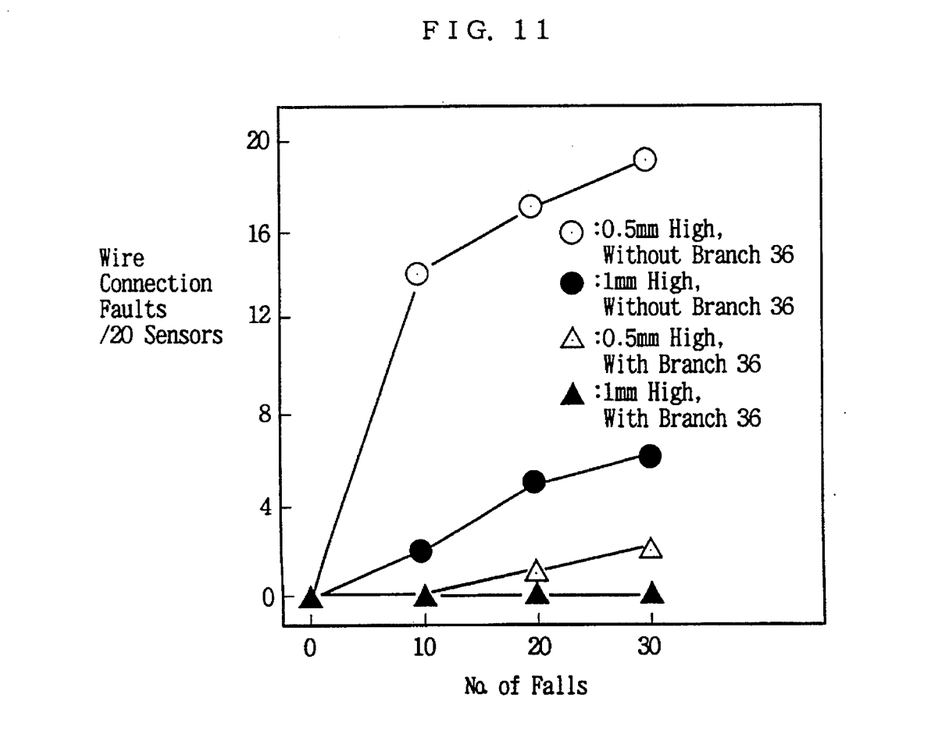
FIG. 11 is a characteristics diagram showing variations in fall resistance due to the absence of a branch 36 from the third embodiment.

FIG. 11 shows the result obtained by causing sensors protected with the housing 58 to fall onto a concrete floor from a position 1 m thereabove. The result is given in terms of the number of samples developing a fault in the connection of the wire 38. The number of sensors in each group tested was 20. The sensor wherein a fault occurred even in one wire 38 was taken as faulty. The same die bonding condition, as well as the same wire bonding condition, was employed for all the sensors in common. Comparison was made between samples having the branch 36 and those not having the branch 36, and between those having a loop height of 0.5 mm and those with a height of 1.0 mm. The samples were 1.5 mm in loop length G. As will be apparent from the diagram, an increase in the loop height from 0.5 mm to 1 mm results in a great decrease in wire connection fault rate, and provision of the branch 36 entails a further decrease in the fault rate. For example, provision of the branch 36 reduces the fault rate substantially to zero when the loop height H is 1.0 mm.

Samples having no branch 36 and 1.5 mm in loop length G were caused to fall 30 times. The resulting wire connection fault rates were 19 out of 20 when the loop height H was 0.5 mm (0.33 in H/G), 10 for H of 0.8 mm (0.53 in H/G), 6 for H of 1.0 mm (0.67 in H/G), 6 for H of 1.5 mm (1 in H/G), and 5 for H of 1.8 mm (1.2 in H/G). On the other hand, when samples wherein H was 2. mm (1.4 in H/G) were tested while being subjected to vibration, the resistance between the frames became unstable, and wire-to-wire contact occurred. Further when samples with G of 2 mm and H of 1.2 mm (0.8 in H/G) were similarly tested, the number of resulting faults was 6 out of 20. Thus, the wire connection fault rate was found relevant to H/G. The above results reveal that H/G should preferably be at least 0.5 to not greater than 1.3.

What we claim is:

1. A semiconductor gas sensor for detecting the presence of a specific gas in a gaseous mixture comprising a sensor main body formed on on the front surface of an insulating substrate having a front surface and a rear surface, the insulating substrate has a rear surface oriented for interface bonding to a frame, where the gas sensor being characterized in that a metal layer is formed over the rear surface of the insulating substrate and heat welded to the frame for die bonding adhesion between the insulating substrate and frame, thereby fastening the insulating substrate to the frame.

2. A gas sensor as defined in claim 1 wherein the metal layer is a gold layer, and a gold plating layer is formed as a top layer on a surface of the frame where said substrate is intended for pending placement, the gold layer over the rear surface Of the insulating substrate being welded to the gold plating layer of the frame.

3. A gas sensor as defined in claim 1 wherein a glass layer is provided as an intermediate layer between the rear surface of the insulating substrate and the metal layer.

4. A gas sensor as defined in claim 3 wherein the frame comprises a multiplicity of frame members, and the insulating substrate is welded to one of the frame members, the frame members being secured to a base, a plurality of electrode pads being provided on the insulating substrate and connected to the sensor main body, the electrode pads being connected to the respective frame members by wire bonding, the frame member having the substrate welded thereto and such frame member being connected to another one of the frame members by a common base for structural support.

5. A gas sensor as defined in claim 3 wherein the frame comprises a multiplicity of frame members, and the insulating substrate is welded to one of the frame members, the frame members being secured to a base, a plurality of electrode pads being provided on the insulating substrate and connected to the sensor main body, the electrode pads being connected to the respective frame members by wire bonding, each of wires used for the wire bonding having a loop height H and a loop length G in a height/length ratio H/G of not smaller than 0.5 to not greater than 1.3.

6. A gas sensor as defined in claim 3 wherein the sensor main body comprises a heater film laid over the full surface area of said main body and two metallic oxide semiconductor films of the same material deposited to cover two different portions across the surface area of said main body, one of the semiconductor films being serviceable for detecting a specific gas of interest, the other semiconductor film selectively permeable to water vapor passage and thereby providing a sensing film being covered with a glass film to detect water vapor.

7. A gas sensor as defined in claim 6 which is useful for detecting a gas and water vapor to be produced or released by food products heated inside cooking devices.

* * * * *

UNITED STATES PATENT AND TRADEMARK OFFICE
CERTIFICATE OF CORRECTION

PATENT NO. : 5,493,897

DATED : February 27, 1996

INVENTOR(S) : NOMURA, et al.

Page 1 of 2

It is certified that error appears in the above-indentified patent and that said Letters Patent is hereby corrected as shown below:

Column 10, line 36, delete "on on" and insert therefor -- on --.

Column 10, line 49, delete "Of" and insert therefor -- of --.

Column 11, line 9, delete "full".

Column 12, lines 3 and 4, delete "the other semiconductor film selectively permeable" and insert therefor -- the other semiconductor film being covered with a glass film selectively permeable --.

UNITED STATES PATENT AND TRADEMARK OFFICE
CERTIFICATE OF CORRECTION

PATENT NO. : 5,493,897

DATED : February 27, 1996

INVENTOR(S) : NOMURA, et al.

It is certified that error appears in the above-indentified patent and that said Letters Patent is hereby corrected as shown below:

Column 12, line 5, delete "being covered with a glass film.

Signed and Sealed this

Seventeenth Day of September, 1996

Attest:

BRUCE LEHMAN

Attesting Officer      Commissioner of Patents and Trademarks